United States Patent
Dodgson et al.

(10) Patent No.: US 6,376,124 B1
(45) Date of Patent: Apr. 23, 2002

(54) ELECTROCHEMICAL CELL

(75) Inventors: John Robert Dodgson, Croydon; Malcolm Trayton Austen, Hayes, both of (GB)

(73) Assignee: Central Research Laboratories, Limited, Hayes (GB)

( * ) Notice: Subject to any disclaimer, the term of this patent is extended or adjusted under 35 U.S.C. 154(b) by 0 days.

(21) Appl. No.: 09/319,447

(22) PCT Filed: Dec. 5, 1997

(86) PCT No.: PCT/GB97/03372

§ 371 Date: Jul. 27, 1999

§ 102(e) Date: Jul. 27, 1999

(87) PCT Pub. No.: WO98/25138

PCT Pub. Date: Jun. 11, 1998

(30) Foreign Application Priority Data

Dec. 7, 1996 (GB) ............................................. 9625464

(51) Int. Cl.⁷ ................................................ H01M 2/02
(52) U.S. Cl. .......................................... 429/127; 429/53
(58) Field of Search .......................... 429/53, 124, 127, 429/131, 136, 139, 163, 231.95, 34; 73/23.2, 1.02

(56) References Cited

U.S. PATENT DOCUMENTS

| | | | | |
|---|---|---|---|---|
| 4,997,732 A | * | 3/1991 | Austin et al. ................. | 429/153 |
| 5,173,376 A | * | 12/1992 | Page et al. .................... | 429/86 |
| 5,486,680 A | * | 1/1996 | Lieberman ................... | 219/211 |
| RE35,746 E | * | 3/1998 | Lake ........................... | 429/127 |
| 6,187,472 B1 | * | 2/2001 | Shiota et al. ................. | 429/127 |

* cited by examiner

Primary Examiner—Gabrielle Brouillette
Assistant Examiner—M. Wills
(74) Attorney, Agent, or Firm—William H. Bollman

(57) ABSTRACT

An electrochemical cell in the form of first and second sheet members (2,12) at least one of which is gas permeable on which is disposed one or more planar electrodes (4,6,8). Peripheral regions of the first and second sheet members (2,12) are sealed together to form a sealed envelope or reservoir containing electrolyte. Electrical connection means (41,61,81) extend from each of the electrodes (4,6,8) across the sealing of the sheet members (2,12) to provide external electrical connection.

25 Claims, 2 Drawing Sheets

ELECTROCHEMICAL CELL

This application is a 371 of PCT/GB97/03372 filed Dec. 5, 1997.

FIELD OF THE INVENTION

This invention relates to electrochemical cells and in particular although, not exclusively to electrochemical cells for use in gas sensors and fuel cells.

BACKGROUND ART

An electrochemical gas sensor for sensing an oxidisible or reducible gas (e.g. carbon monoxide) in the atmosphere usually contains a sensing or working electrode, a counter electrode and an inlet (usually a diffusion barrier) to allow the atmosphere to permeate to the sensing electrode. Both electrodes are in contact with an electrolyte in order firstly to produce an electrochemical reaction at the sensing electrode with the gas to be sensed, and secondly to produce an electrochemical reaction at the counter electrode with oxygen in the atmosphere, electrolyte or other gas source. Current is carried through the electrolyte by ions produced in the reaction and by electrons through an external circuit, the current in the circuit indicating the gas concentration. A reference electrode may be employed in combination with a potentiostat circuit to maintain the potential between the sensing electrode and the cell electrolyte in order to increase stability of operation.

In terms of physical construction, the sensor normally comprises an external housing which acts as a reservoir for the electrolyte, a wick or matrix to hold the electrolyte in contact with the electrodes, and external electrical terminals making electrical connection with the electrodes. The majority of present sensor cells use a stacked electrode arrangement, as for example in U.S. Pat. No. 4,406,770.

There has been recent proposals for design simplification, see for example U.S. Pat. No. 5,183,550 which discloses a gas sensor in which the sensing, counter and reference electrodes are mounted in a common plane on a common ceramic substrate, with contact leads extending from the electrodes to the other surface of the substrate for electrical connection.

Our copending application WO 96/14576 (our ref. PQ12622) discloses and claims a gas sensor comprising a substrate, electrodes formed as porous planar elements on the substrate, and the substrate being porous to permit permeation of gas to the electrodes from the environment, a housing containing a reservoir of electrolyte and external terminals mounted to the housing, wherein the substrate is bonded to the housing by the application of pressure and heat, so that in a single assembly operation, the housing is sealed and electrical connections are made to the electrodes while blocking the porosity of the electrodes to prevent electrolyte permeating through the electrode to the area of the electrical connection.

While the above construction represents a considerable advance in terms of cost reduction, nevertheless inexorable demands for cost reduction without sacrificing quality, forces further design simplifications.

SUMMARY OF THE INVENTION

This invention is based on a concept of providing two flexible plastics sheets, one having electrode areas printed thereon, which are bonded together around their edges to form a reservoir for electrolyte, rather in the form of a tea bag.

Accordingly, the present invention provides in a first aspect, an electrochemical cell comprising at least first and second sheet members, at least one of the sheet members including a gas permeable section on which is disposed one or more planar electrodes, peripheral regions of the first and second sheet members being sealed together to form a reservoir containing electrolyte, and including electrical connection means extending from each of said electrodes across the sealing of the sheet members for external electrical connection.

In a further aspect, the invention provides an electrochemical cell assembly formed of a plurality of sections, each section having first and second, sheet members, each sheet member including a gas permeable region on which is disposed a planar electrode, peripheral regions of the first and second sheet members being sealed together to form a reservoir containing electrolyte, and including electrical connection means extending from said electrodes across the sealing of the sheet members for external electrical connection, said assembly including manifold means for directing first and second gases to each section so as to contact respective first and second sheet members.

In the latter embodiment of the invention, by forming the electrodes on different sheet members, it is possible to arrange a first gas to flow over the first sheet member, and a second gas over the second sheet member. For example with a suitable manifold structure, the assembly may constitute a fuel cell.

The construction of the present invention, either as a gas sensor or fuel cell, is extremely simple and permits substantial cost savings.

Various specific forms of construction are possible. Both sheet members may be flexible, the flexibility permitting the insertion of electrolyte between them. Both sheet members may be part of a single sheet, which is folded over so that the sheet members are face to face. Alternatively one or both sheet members may be formed from a sheet which is performed to have a three dimensional shape, for example one sheet may have a well formed therein to define a reservoir space. Alternatively in one preferred construction, one sheet may be formed as a planar sheet of porous PTFE carrying the required configuration of electrodes, and a flexible plastics closure sheet may be welded to the edges of the PTFE sheet to define the reservoir.

A third sheet member may also be employed, for example an intermediate layer of lower melting point for sealing the two outer sheets. The third sheet may be of highly porous material to hold the electrolyte. In a further form, the third sheet member may define a second reservoir space for a second electrochemical cell.

The invention thus permits very thin assemblies (of the order of 1 to 2 mm) to be produced in a variety of shapes. This permits applications for a gas sensor where space is extremely limited, e.g. on or in a person's clothing. The extreme cheapness of production provides the possibility of "disposable" sensors which may be used only once or a small number of times and then disposed of.

Thus production and assembly may be simplified by printing the electrodes on a sheet of flexible substrate material which then is folded over one or more times, or placed against another sheet of material and then sealed around the edges to form a "tea bag" type structure. The wick and electrolyte are contained within the bag and the sealing may be by heat, adhesive or mechanical force. Such devices may be made in irregular shapes, and are suitable for high levels of automation for cost reduction.

Where sensors of a completely flexible construction are produced, they will in practice normally be attached to a rigid support or mounted in a rigid housing to prevent spurious noise due to bending. Due to the compact nature of the thin sensor, it may be disposed with control electronics on to a single substrate. This substrate may also have the diffusion-limiting gas access built in.

The electrochemical cells in accordance with the invention lend themselves to automatic fabrication and assembly on a production line. Thus sheet material stored in one or more rolls can be unwound and superimposed, and a pattern of cells then pressed, cut and sealed in simultaneous operations from the sheets. For a fuel cell, the cells may be formed as flat arrays, e.g. 4×4 on the sheets.

While the electrolyte in the cells is usually in the form of a liquid, it may be in the form of a gel or solid polymer, pasted or otherwise affixed to the electrodes.

For an electrode printed on a gas permeable membrane three functions have to be achieved to assemble it into an electrochemical cell: 1) to mechanically attach the electrode, 2) seal in the electrolyte and 3) to provide a conductive path from the electrode to the outside of the cell.

A preferred construction method, similar to that as described in WO 96/14576 uses the technique of heat sealing a porous PTFE sheet member (the electrode) to the cell body component As the printed electrode runs through this seal all three needs are met with the addition of no extra components and in addition the ability to automate is provided.

The sheet members may also be glued together; this method can achieve all three requirements for cell assembly. In practice it makes use of the porosity of a PTFE membrane to achieve adhesion. This method of construction is important to allow the assembly of fragile or complex electrodes. Fragile electrodes may result from cost reduction, for example. Complex electrodes include irregular shapes, multiple prints or sealing in more than one plane e.g. around the outside of a moulding. This assembly method may be important for small disposable sensors (limited life). Advantages: very little disruption of the electrode ink structure, the adhesive can enter the porosity of the electrode ink and substrate increasing strength, and the method is very adaptable. With this method, different methods of electrical connection to the electrodes may be employed, for example electrode lead wires extending from the electrodes to external electrical connections.

The ability to produce multiple cell assemblies at low cost is ideal for fuel cell fabrication. The production of cells in a strip form may be adapted to give an array (say 3×4), this array forming a single layer in a stacked assembly. One electrode of each cell is on the top of the layer and the other underneath, to allow the air and fuel gases to be supplied via simple manifold systems to the relevant electrode.

A preferred stacked assembly includes rigid spacer devices interleaved with the layers of cells and providing a manifold structure on each side of each layer to permit inflow of an appropriate gas. First manifolds on one side of the layer are disposed to allow inflow of a fist gas from one direction and second manifolds are disposed on the other side of the layer are arranged at right angles to the first manifolds to allow inflow of a second gas from a direction at right angles to the first By adjusting the size and shape of the manifolds the volume or flow rate of the two gases could be set as desired.

In each layer the cells may be connected in series to dictate the voltage generated by the cell, and the layers may be connected together in parallel in order to define the maximum current of the assembly.

A second stack assembly is to have all the layers fabricated in one long strip which is folded up in a "zigzag" pattern. A rigid manifold/spacer arrangement is employed to permit air flow through the stack at right angles to the fold pattern.

In the case of a fuel cell, it is possible that the sheet members may not be completely sealed around their peripheries, but that a small unsealed region may be provided in order to provide a vent for water or other liquid generated during operation within the cell.

BRIEF DESCRIPTION OF THE DRAWINGS

A preferred embodiment of the invention will now be described with reference to the accompanying drawings wherein.

DESCRIPTION OF THE PREFERRED EMBODIMENTS

Figure 1:
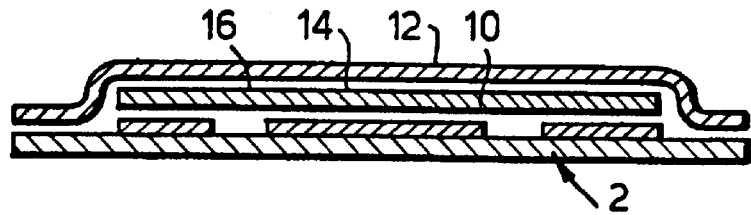
FIG. 1 is a sectional view of an embodiment of an electrochemical cell for use as a gas sensor in accordance with the invention.
Figure 2:
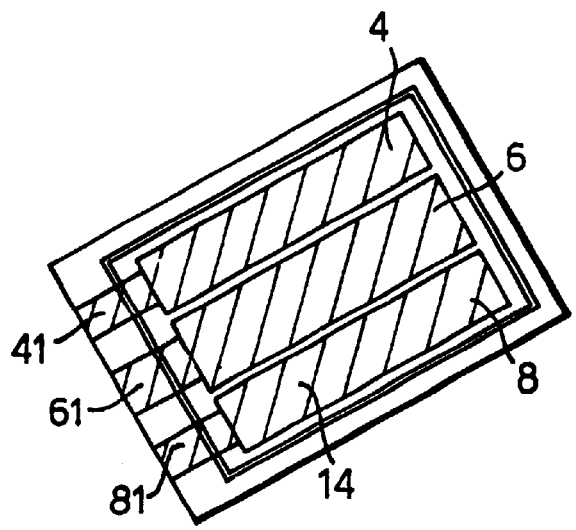
FIG. 2 is a plan view of the sensor of FIG. 1.

Referring now to FIGS. 1 and 2, there is shown an electrochemical cell in the form of a gas sensor comprising a flexible porous PITE substrate 2, 0.25 mm thick onto which are printed a reference electrode 4, a working electrode 6, and a counter electrode 8. As shown in FIG. 2, these electrodes are generally rectangular and are disposed side by side with the working electrode 6 disposed in the centre so that the reference and counter electrodes can perform their functions without interfering one with the other. Portions of the printed electrodes 41, 61, 81 extend to one edge of substrate 2 for making external electrical connection.

The electrodes are deposited onto the substrate 2 by, for example, screen printing, suction or vacuum depositing selected areas from a suspension placed onto the substrate, spray coating, or any other method suitable for producing a patterned deposition of solid material. Deposition may be of a single material or of more than one material sequentially in layers, so as, for example, to vary the properties of the electrode material through its thickness or to add a second layer of increased electrical conductivity above or below the layer which is the main site of gas reaction.

The electrodes are printed on to a gas impermeable substrate 2 which is self supporting. This has the advantage of making the electrode stiffer and so less susceptible to vibration and shock and makes it more difficult to rupture or pierce the electrode.

A wick 10 of a highly absorbent material and containing a charge of electrolyte liquid or gel is positioned over the electrodes, and a flexible plastics sheet 12 of polypropylene, 0.1 mm thick, having a lower melting point than PTFE, is positioned over the wick and substrate to define a reservoir space 14 for the electrolyte. Sheet 12 has the same shape and size as that of sheet 2 in plan, and the edges of the sheets are bonded together in a rectangular bond line 16 by an appropriate pressing tool which applies suitable heat and pressure to the to effect the bond. In the region where the bond extends over the connecting regions 41, 61, 81, the sealing process causes the porosity of the electrode material to be blocked, which forms a barrier to the egress of electrolyte from the wick 10. The resultant sensor has a thickness which is not greater than 2 mm.

In use, gas to be sensed permeates through the PTFE substrate 2 to the working electrode 6. The rate of diffusion of the gas to be sensed is controlled by the porosity of the substrate 2 so the substrate becomes the diffuser control for the cell.

Figure 3:
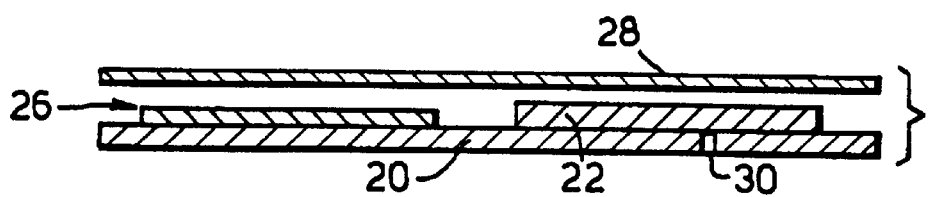
FIG. 3 is a sectional exploded view of the gas sensor of FIGS. 1 and 2 incorporated in a gas sensor for personal use.

Referring now to FIG. 3, this shows an electrochemical cell suitable for use as a gas sensor designed for personal use in the form of a card which may be placed in the pocket of a person's clothing or attached to the exterior of the clothing. The card comprises a stiff plastics substrate 20 on which is mounted a electrochemical cell 22, of the form shown in FIGS. 1 and 2. An electronics chip 26 is also mounted on substrate 20 and is electrically connected to the cell 22. The electronics chip 26 is manufactured by a CMOS process and provides a power supply (a battery or solar powered cell is provided), control circuitry for energising the electrodes of the cell and output means to provide an alarm signal. A cover 28 is provided for covering the cell 22 and chip 26. An aperture 30 is provided in the substrate for diffusion— limited gas access to the PTFE substrate 2 of the cell 22.

Figure 4:
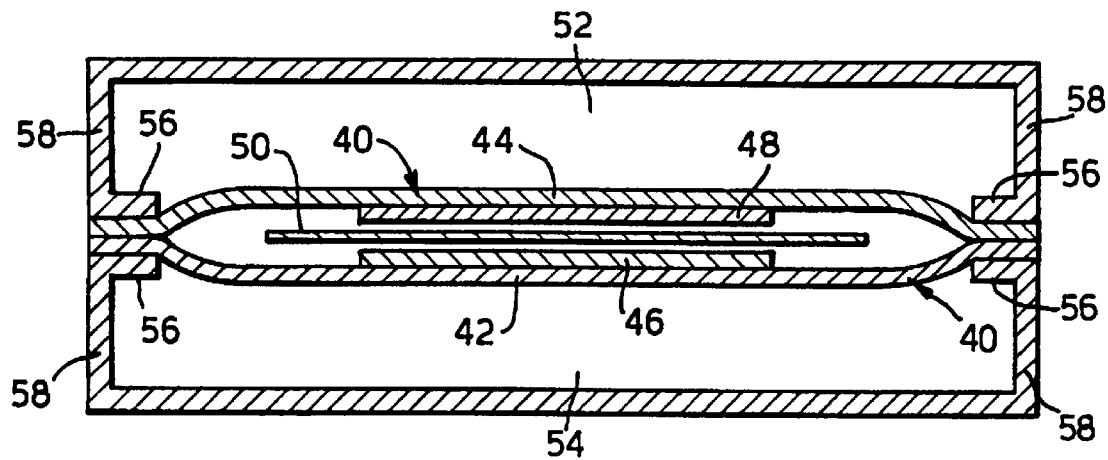
FIG. 4 is a sectional view of an embodiment of an electrochemical cell for use as a fuel cell element in accordance with the invention.
Figure 5:
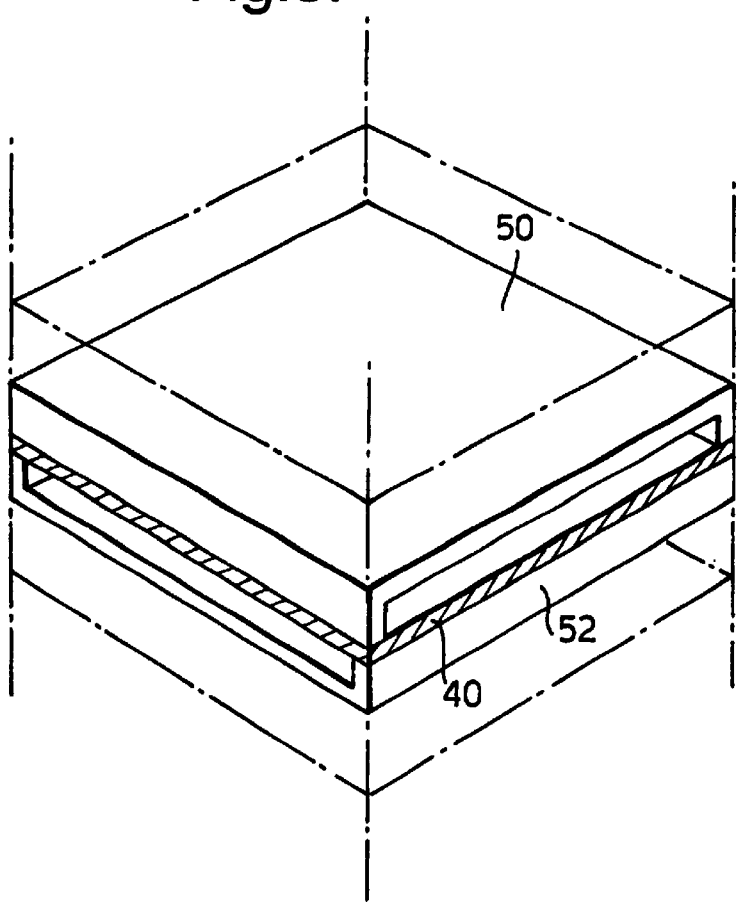
FIG. 5 is a perspective view of part of the fuel cell element of FIG. 4, showing the how the element is mounted in a fuel cell stack of such elements.

Referring now to FIGS. 4 and 5, there is shown an electrochemical cell 40 for use in a fuel cell constructed in accordance with the present invention. The cell 40 comprises first and second flexible sheets 42, 44, each being formed of gas permeable PTFE and on each inside surface of which is printed a respective electrode area 46, 48. A wick 50 containing a charge of electrolyte material is disposed between the electrodes. The two sheets 42, 44 are rectangular in configuration and are bonded to one another along their four edges to form a sealed envelope, or reservoir is for the electrolyte. Although not shown in the drawings, portions of the electrode areas extend through the bonded region to the edges of the sheets for external electrical connection in a similar way to that shown in FIGS. 1 and 2. First and second rectangular gas manifolds 52, 54 are placed above and below the fuel cell element 40 with flanges 56 of side walls 58 clamping the cell 40 between the manifolds. The manifolds permit gas access of first and second gases; one gas usually being fuel and the other air respectively to the each side of the cell 40. The fuel and aim diffuse through the respective sheets 42, 44 and react with the respective electrode 46, 48. Thus electrochemical reactions are created at the electrodes 46, 48, generating an electrical output at the external electrical connections.

As indicated in FIG. 5, a multiplicity of cells 40 are stacked in a vertical stack 60, a first gas entering the stack from one side 62 of the stack at right angles to a side 64 at which a second gas enters. External connections to the cells 40 are interconnected so as to provide a combined electrical output from the stack of cells 40.

What is claimed is:

1. A gas sensor consisting of an electrochemical cell, comprising:
    a first sheet member having thereon a gas permeable section, said gas permeable section having disposed thereon a plurality of planar electrodes;
    a second sheet member,
    wherein peripheral regions of said first sheet member and said second sheet member being sealed together to form a reservoir therebetween, said reservoir being adapted to contain electrolyte; and
    electrical connection means extending from each of said plurality of planar electrodes to said peripheral regions of said first sheet member and said second sheet member, said electrical connection means being adapted to provide a respective external electrical connections for said plurality of planar electrodes.

2. A gas sensor consisting of an electrochemical cell according to claim 1, further comprising:
    a third sheet member disposed between said first sheet member and said second sheet member.

3. A gas sensor consisting of an electrochemical cell according to claim 1, further comprising:
    a third sheet member having peripheral regions thereof being sealed to said first sheet member and said second sheet member to define a second reservoir.

4. A gas sensor consisting of an electrochemical cell according to claim 1, wherein:
    said first sheet member comprises:
        a flat porous PTFE sheet having said plurality of planar electrodes formed thereon, and
    wherein said second sheet member comprises:
        a flexible plastic sheet.

5. A gas sensor consisting of an electrochemical cell according to claim 1, wherein:
    said plurality of planar electrodes comprises:
        a first electrode;
        a second electrode; and
        a third electrode,
        wherein said first electrode, said second electrode and said third electrode are disposed side by side on said first sheet member.

6. A gas sensor consisting of an electrochemical cell according to claim 1, further comprising:
    a stiff planar substrate member having mounted thereon said reservoir formed by said first sheet member and said second sheet member, and a electrical circuit means adapted to operate said electrochemical cell as a gas sensor.

7. A gas sensor consisting of an electrochemical cell according to claim 1, wherein:
    said peripheral regions of said first sheet member and said second sheet member are sealed together by application of pressure and heat.

8. A gas sensor consisting of an electrochemical cell according to claim 1, wherein:
    each of said plurality of planar electrodes has a portion extending through said sealed together peripheral regions of said first sheet member and said second sheet member to define said electrical connection means.

9. A gas sensor consisting of an electrochemical cell according to claim 1, wherein:
    said electrolyte is a liquid electrolyte, and is held in a porous member.

10. A gas sensor consisting of an electrochemical cell according to claim 1, wherein:
    said electrolyte is a gel electrolyte, and is affixed to surfaces of said plurality of planar electrodes.

11. A gas sensor consisting of an electrochemical cell according to claim 1, wherein:
    said electrolyte is a polymer electrolyte, and is affixed to surfaces of said plurality of planar electrodes.

12. A gas sensor consisting of an electrochemical cell assembly, comprising:
    a plurality of sections; and
    manifold means, wherein each of said plurality of sections comprises:
a first sheet member; and
a second sheet member,
wherein each of said first sheet member and said second sheet member has a gas permeable region on which at least one planar electrode is disposed, peripheral regions of said first sheet member and said second sheet member being sealed together to form a reservoir therebetween adapted to contain electrolyte,
wherein each of said plurality of sections has electrical connection means extending from said at least one planar electrode across said sealed together peripheral regions of said first sheet member and said second sheet member, said electrical connection means providing external electrical connection, and
wherein said manifold means directs a first gas and a second gas to each of said plurality of sections, said first gas being directed to contact one of said first sheet member of respective one of said plurality of sections, and said second gas being directed to contact said second sheet member of said respective one of said plurality of sections.

13. A gas sensor consisting of an electrochemical cell assembly according to claim 12, wherein:
each of said first sheet member and said second sheet member comprises:
a PTFE sheet.

14. A gas sensor consisting of an electrochemical cell assembly according to claim 12, wherein:
said plurality of sections are arranged in a rectangular matrix to define a plurality of fuel cell elements.

15. A gas sensor consisting of an electrochemical cell assembly according to claim 12, wherein:
said plurality of sections are arranged in a single row to define a plurality of fuel cell elements.

16. A gas sensor consisting of an electrochemical cell assembly according to claim 14, wherein:
each of said plurality of sections are stacked on top of each other.

17. A gas sensor consisting of an electrochemical cell assembly according to claim 15, wherein:
said plurality of sections arranged in a single row is folded to place at least one of said plurality of fuel cell elements on top of another one of said plurality of fuel cell elements.

18. A gas sensor consisting of an electrochemical cell assembly according to claim 12, wherein:
each said plurality of sections comprises:
a matrix of fuel cells, and
wherein each of said plurality of sections are stacked on top of each other.

19. A gas sensor consisting of an electrochemical cell assembly according to claim 12, wherein:
each said plurality of sections comprises:
rigid spacer means for defining said manifold means for each of said plurality of sections.

20. A gas sensor consisting of an electrochemical cell assembly according to claim 12, wherein:
said manifold means is arranged to direct said first gas and said second gas from opposite sides of said first sheet member and said second sheet member, respectively.

21. A gas sensor consisting of an electrochemical cell assembly according to claim 12, wherein:
said peripheral regions of said first sheet member and said second sheet member are sealed together by applying pressure and heat.

22. A gas sensor consisting of an electrochemical cell assembly according to claim 12, wherein:
said at least one planar electrodes has a portion extending through said sealed together peripheral regions of said first sheet member and said second sheet member to define said electrical connection means.

23. A gas sensor consisting of an electrochemical cell assembly according to claim 12, wherein:
said electrolyte is a liquid electrolyte, and is held in a porous member.

24. A gas sensor consisting of an electrochemical cell assembly according to claim 12, wherein:
said electrolyte is a gel electrolyte, and is affixed to surfaces of said plurality of planar electrodes.

25. A gas sensor consisting of an electrochemical cell assembly according to claim 12, wherein:
said electrolyte is a polymer electrolyte, and is affixed to surfaces of said plurality of planar electrodes.

* * * * *